United States Patent [19]

Warriner

[11] Plant 5,121

[45] Oct. 18, 1983

[54] ROSE PLANT JACGOLD OF THE HYBRID TEA CLASS

[75] Inventor: William A. Warriner, Tustin, Calif.

[73] Assignee: Jackson & Perkins Company, Medford, Oreg.

[21] Appl. No.: 353,521

[22] Filed: Mar. 1, 1982

[51] Int. Cl.[3] ..... A01H 5/00

[52] U.S. Cl. ..... Plt./15

[58] Field of Search ..... Plt./15

*Primary Examiner*—Robert E. Bagwill

*Attorney, Agent, or Firm*—Klarquist, Sparkman, Campbell, Leigh, Whinston & Dellett

[57] ABSTRACT

A hybrid tea rose variety having a vigorous, upright plant producing straight stems; pointed yellow buds; glossy, dark green foliage; absence of prickles on lower edges of rachis.

1 Drawing Figure

This present invention relates to a new and distinct variety of rose plant named Jacgold of the hybrid tea class which was originated by me by crossing an unnamed variety with the variety Sunshine, U.S. Plant Pat. No. 3,791.

The primary objective of this breeding was to produce a new rose variety suitable for the production of cut blooms when grown in a greenhouse. This objective was substantially achieved along with other desirable improvements as evidenced by the following unique combination of characteristics which are outstanding in the new variety and which distinguish it from its parents as well as from all other varieties of which I am aware:

1. A vigorous, upright plant producing very straight stems, mostly of a length of 18 inches to 30 inches.
2. Pointed yellow buds, darker than those of the variety Emblem (JP 76-5492) and faded less.
3. Foliage more glossy and slightly darker color than that of Emblem.
4. High degree of resistance to rose powdery mildew.
5. Absence of prickles on lower edges of rachis.

Asexual reproduction of this new variety by budding, as performed at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color terminology in accordance with The Royal Horticultural Society Colour Chart except where ordinary dictionary significance of color is indicated.

Parentage:

*Seed parent.*—Unnamed variety.

*Pollen parent.*—Sunshine, U.S. Plant Pat. No. 3,791.

Classification:

*Botanical.*—Rosa hybrid.

*Commercial.*—Hybrid tea.

FLOWER

Observations made from plants grown in greenhouse at Irvine, Calif., in November 1981.

Blooming habit: Continuous.

Bud:

*Size.*—1½" to 1¾" when petals start to unfurl.

*Form.*—Long, pointed ovoid.

*Color.*—When sepals first divide, Yellow-Orange 16A; when half blown; upper side of petals Yellow-Orange 16A; lower side of petals Yellow-Orange 16A.

*Sepals.*—Color: Outer surface Green 138B; smooth surface; three appendaged sepals lightly appendaged; two unappendaged sepals hairy edge and a few glands.

*Receptacle.*—Color: Green 138B. Shape: Funnel. Size: Small. Surface: Smooth.

*Peduncle.*—Length: Medium. Surface: Smooth, slightly glandular. Color: Medium green. Strength: Stiff, erect.

*Opening.*—Petals curl back, slightly pointed.

Bloom:

*Size.*—Large. Average open size 4" to 4½".

*Borne.*—Singly.

*Stems.*—Long, strong.

*Form.*—When first open, high center. Permanence: Retains its form to the end.

*Petalage.*—Number of petals under normal conditions: 35–40.

*Color.*—Center of flower: Upper side of petals Yellow-Orange 16A. Reverse side of petals Yellow-Orange 16A. Base of petals Yellow-Orange 16A. General tonality from a distance: Yellow-Orange 16A.

*Variegations.*—Occasional very light vegetative green area at midrib of outer petals.

*Discoloration.*—General tonality at end of first day, none; third day, lighter shades of yellow near Yellow-Orange 15C.

*Fragrance.*—Slight.

Petals:

*Texture.*—Thick.

*Shape.*—Round.

*Form.*—Edges slightly quilled.

*Arrangement.*—Imbricated. Petaloids: Few.

*Persistence.*—Drop off cleanly.

*Lastingness.*—On the plant, long. As cut flowers, long.

Reproductive parts:

*Anthers.*—Large. Color: White. Arrangement: Regular around styles.

*Filaments.*—Color: Yellow and reddish.
*Pollen.*—Gold yellow.
*Styles.*—Color: Very pale green at base, pink at distal half.
*Stigmas.*—Color: Very pale yellow.

PLANT

Form: Bush.
Growth: Vigorous, upright, stems tend to be very straight.
Foliage: Number of leaflets on normal mid-stem leaves: 5 or 7.
*Size.*—Large.
*Quantity.*—Normal.
*Color.*—New foliage: Light green overlaid with Greyed purple 183D. Old foliage: Dark green 136A.
Leaflets:
*Shape.*—Oval pointed.
*Texture.*—Glossy.
*Edge.*—Serrated.
*Serration.*—Single.
*Petiole.*—Rachis: Color, green. Underside: Smooth.

*Stipules.*—Long, bearded.
*Disease resistance.*—Resistant to mildew under normal growing conditions at Irvine, Calif.
Wood:
*New wood.*—Color: Light green. Bark: Smooth.
*Old wood.*—Color: Green. Bark: Smooth.
Prickles:
*Quantity.*—On main stalks from base, ordinary. On laterals from stalk, ordinary.
*Form.*—Long base. Long, hooked downward.
*Color when young.*—Green and red.
*Position.*—Irregular.
Small prickles:
*Quantity.*—On main stalks, none. On laterals, none.

I claim:

1. A new and distinct variety of rose plant of the hybrid tea class, substantially as herein shown and described, characterized particularly as to novelty by the unique combination of deep yellow, pointed buds born on long straight stems, with glossy mildew resistent foliage, no prickles on rachises.

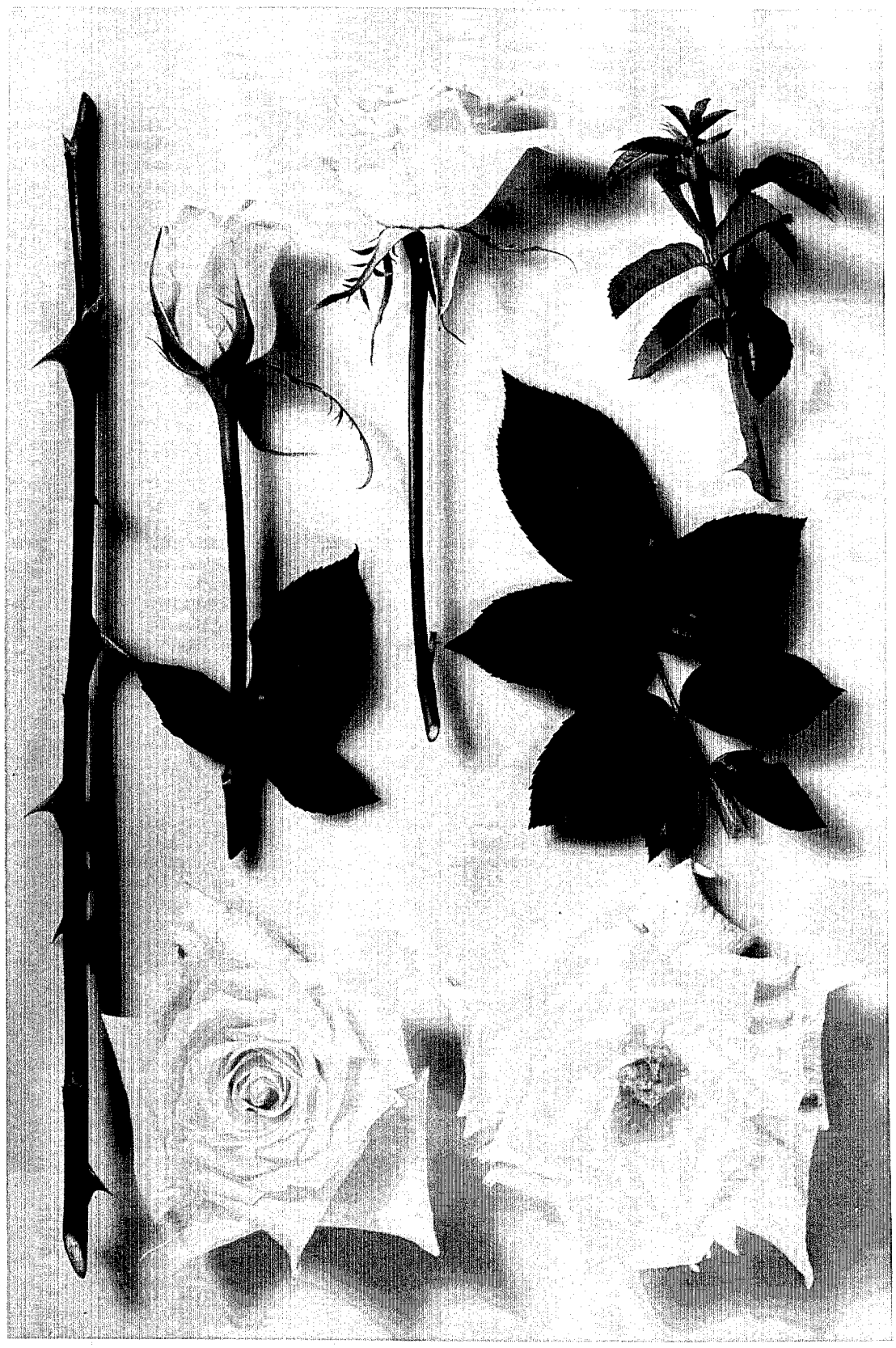

* * * * *